(12) United States Patent
Grigoropoulos (10) Patent No.: US 11,083,459 B2
(45) Date of Patent: Aug. 10, 2021

(54) APICAL SURGICAL WOUND DEBRIDEMENT

(71) Applicant: Katerina Grigoropoulos, Skokie, IL (US)

(72) Inventor: Katerina Grigoropoulos, Skokie, IL (US)

( * ) Notice: Subject to any disclaimer, the term of this patent is extended or adjusted under 35 U.S.C. 154(b) by 314 days.

(21) Appl. No.: 16/415,481

(22) Filed: May 17, 2019

(65) Prior Publication Data

US 2020/0360019 A1 Nov. 19, 2020

(51) Int. Cl.
*A61F 13/00* (2006.01)
*A61B 17/08* (2006.01)
*A61F 13/02* (2006.01)

(52) U.S. Cl.
CPC ........ *A61B 17/085* (2013.01); *A61F 13/0236* (2013.01); *A61F 2013/0028* (2013.01)

(58) Field of Classification Search
CPC ......... A61F 13/0236; A61F 2013/0028; A61B 17/085
USPC ....................................................... 606/216
See application file for complete search history.

(56) References Cited

U.S. PATENT DOCUMENTS

| 4,778,679 | A | * | 10/1988 | Silvetti | ................ | A61K 31/715 |
| | | | | | | 424/648 |
| 5,447,505 | A | * | 9/1995 | Valentine | ................ | A61L 15/24 |
| | | | | | | 602/48 |
| 5,648,141 | A | * | 7/1997 | Butterworth | ............ | A61F 13/36 |
| | | | | | | 428/131 |
| 6,669,966 | B1 | * | 12/2003 | Antelman | ............... | A61P 15/00 |
| | | | | | | 424/635 |
| 8,377,016 | B2 | * | 2/2013 | Argenta | .................. | A61M 1/90 |
| | | | | | | 604/305 |
| 2002/0173807 | A1 | * | 11/2002 | Jacobs | ................... | A61B 17/11 |
| | | | | | | 606/151 |
| 2003/0050590 | A1 | * | 3/2003 | Kirsch | .................... | C08L 35/04 |
| | | | | | | 602/52 |
| 2005/0182443 | A1 | * | 8/2005 | Jonn | ................ | A61B 17/00491 |
| | | | | | | 606/213 |
| 2017/0014483 | A1 | * | 1/2017 | Lynch | .................. | A61K 9/0024 |
| 2021/0023024 | A1 | * | 1/2021 | Purvis | ................. | A61L 26/0066 |

FOREIGN PATENT DOCUMENTS

DE       102004039514 A1 *  2/2006  ........... A61B 17/085

OTHER PUBLICATIONS

Butler, N.P, Apical Debridement—A Hypothesis and Preliminary Report, Oct. 1970, International Endodontic Journal, vol. 4, Issue 4, pp. 52-56 (Year: 1970).*
3M Steri-Strip S surgical Skin Closure Commonly Asked Questions, pp. 1-8, 2006. (Year: 2006).*

(Continued)

*Primary Examiner* — Kim M Lewis (57) ABSTRACT

Apical wound debridement methods for wound healing provides a geometry of the wound area that enhances healing, either when using these methods alone or in combination with other wound healing grafts and medical devices. Further, the wound healing is used at a variety of locations where wounds are found, such as but not limited to the foot, ankle, leg, back, neck, arms, hands and face.

27 Claims, 10 Drawing Sheets

(56) References Cited

OTHER PUBLICATIONS

Von Arx, Thomas, Apical surgery: a Review of current techniques and outcome, 2011 Journal List Saud Dent J, v23(1); PMC3770245 https://www.ncbi.nlm.nih.gov/pmc/artices/PMC3770245 (Year: 2011).*
Belken, Thomas et al., Current and Emerging Modalities in Wound Debridement, 2013, vol. 26—Issue 8, pp. 32-38 (Year: 2013).*
Klein, Robert, The Importance of Aggressive Wound Debridement to Aid in Healing, 2019 https://www.woundcarelearningnetwork.com/poster/importance-aggressive-wound-debridement-aid-healing (Year: 2019).*
Debridement https://surgery.ucsf.edu/conditions--procedures/debridement.aspx (Year: 2021).*
Brem H, Stojadinovic O, Diegelmann RF, et al.,"Molecular markers in patients with chronic wounds to guide surgical debridement," Mol Med. 2007;13(1-2):30-9.
Sarrafian et al., "Cross-Sectional and Topographic Anatomy," https://musculoskeletalkey.com/cross-sectional-and-topographic-anatomy, May 28, 2016.

* cited by examiner

Figure 6: DM male with left hallux wound sustained after wearing ill-fitting boots Figure 7: 71 yo DM male with right foot dehiscence after first ray amputation Figure 8: 77 yo DM male with dehiscence after hardware removal Figure 9: 59 yo DM male with dehiscence after right fifth ray amputation Figure 10: 67 yo DM male with recurrent right plantar ulceration after TMA

APICAL SURGICAL WOUND DEBRIDEMENT

BACKGROUND OF THE INVENTION

The treatment of wound care has become a crucial necessity in the healthcare system, especially with the significant rise in diabetes. Various comorbidities inhibit and prolong the process of healing thereby ultimately leading to the development of chronic wounds. This results in a significant burden to patients and the health care system. An average of 6.5 million patients in the US are affected with chronic wounds every year, with this number rising annually [1]. Chronic wounds cost the US medical system an average of $25 billion yearly to manage and treat these wounds [1]. With the health and financial burden for treating such wounds, it is beneficial to understand not only the complex physiology behind wound healing but also effective treatments, namely more effective surgical wound debridement.

Wound care is a multifaceted service that incorporates various modalities including wound dressings, skin substitutes, hyperbaric oxygen, negative pressure vacuum therapy and wound debridement. Debridement techniques include both surgical and non-surgical methods. Although the literature defines surgical debridement as the sharp removal of biofilm, fibrotic, and necrotic tissue from wounds, there is little guidance and research behind the technique of surgical debridement.

It is common practice to remove all visible non-viable tissue and debride to the point of a healthy bleeding base with caution not to comprise the surrounding healthy tissue. The purpose of debriding the wound base and edges is to remove any biofilm that may impede wound healing and to re-injure the site and re-instigate the inflammatory phase. Inflammation brings forth cytokines, growth factors, nutrients and enzymes to promote further healing by creating an environment suitable for anabolic metabolism.

There is very little literature regarding the techniques behind surgical wound debridement. The standard of practice is to debride to the point of bleeding wound edges and base. Although this technique does serve a purpose, a more aggressive debridement has multiple benefits when it comes to wound care and wound healing. In theory, the more extensive the injury, the more growth factors and nutrients will flood to the injured site surrounding the wound. This could potentially create a more inducible environment for healing for not only the freshly debrided healthy tissue but the chronic wound as well.

Additionally, another potential theory is that an aggressive debridement reduces polar wound edge tension which facilitates wound geometry manipulation. In theory, a linear wound heals faster than one that is more circular in nature. This technique named "apical surgical wound debridement" is a debridement technique more aggressive than the "normal" standard of care. Apical debridement not only creates a more inducible wound healing environment by bringing forth more growth factors and nutrients but also facilitates the manipulation of wound geometry.

SUMMARY OF INVENTION

The present invention relates to methods for treating wounds by using apical debridement. This comprises a method that utilizes a wedge excision at the most polar extreme ends of a wound. This surgical wedge excision relieves tension to the wound perimeter and allows the manipulation of wound geometry by creating a more malleable wound border. With this periwound tension relaxation, the skin edges at the most extreme ends of the wound are closer thereby encouraging epithelial cell migration between the wound edges. This, thus, facilitates wound closure.

In addition, applying tension towards the wound from opposite directions with steristrips, further relaxes the wound edges and acts as a "wound splint" to limit skin edge movement, frictional forces and potential damage to the newly formed epithelial cells. Therefore, the present invention includes the addition of these strips. The steristrip application step comprises applying bidirectional opposing tension towards the wound by manual manipulation and applying steristrip across the wound to secure this position and allow the wound edges to rest in closer proximity Additionally, applying skin tension towards the wound from opposite directions using the steristrip technique further relaxes the wound edges and acts as a wound splint to limit skin edge movement, frictional forces and potential damage to the newly formed epithelial cells.

The present invention relates to methods of enhancing wound healing. This invention also relates to a method for advancing wound care grafts.

DETAILED DESCRIPTION OF THE INVENTION

Figure 1:
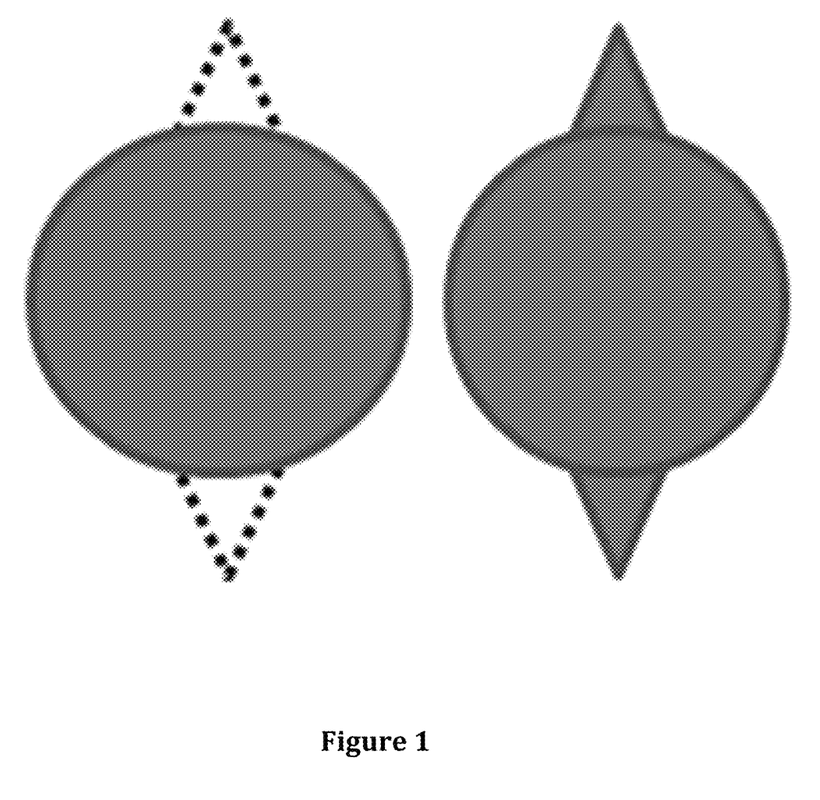
FIG. 1: Illustrates the direction of apex debridement at the two most extreme ends of a wound.

The dotted line in FIG. 1 represents the apex debridement at the two most extreme ends of a wound. Although there is more damage to the surrounding healthy and viable soft tissue, there is a geometrical benefit that can transform a circular wound to one that is more linear in nature. The method of the present invention strives for the geometry illustrated in FIG. 1.

The location and width/height of apical excision depends on the size of the wound and its location compared to the natural skin lines of the integument. The best way to determined that natural flow of the integumental lines is to pinch the periwound towards the wound and visualize the skin lines as demonstrated by the black arrows in FIG. 2.

Figure 3:
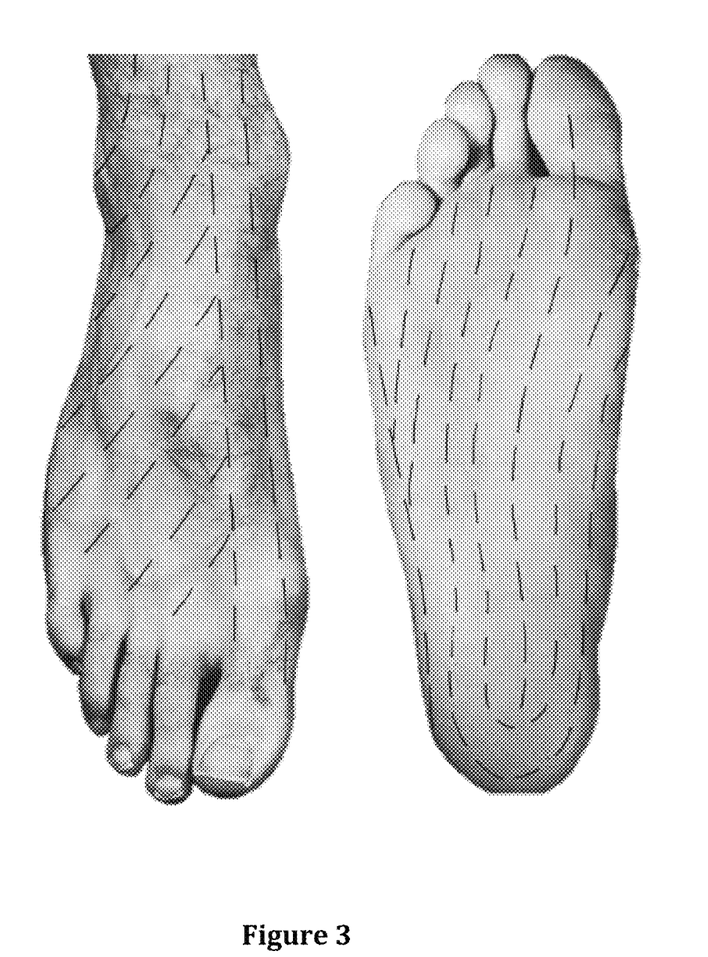
FIG. 3: Illustrates the natural skin lines of the foot.

By pinching the periwound, the natural skin lines become more apparent and guide the direction of the apical excision. The apex of the excision should be parallel to the natural skin lines. Excision along the parallel directions of the skin lines allows easer geometrical manipulation and accelerated healing compared to apical excision perpendicular to the skin lines. The natural skin lines of the foot are noted in FIG. 3. The cleavage lines on the dorsal, medial aspects of the foot are parallel to the media border with more lateral deviation of the skin lines past the first ray of the foot. On the plantar surface, the lines have a linear formation proximal to distal with slight medial deviation along the lateral aspect. Using these natural skin lines as a template for apical excision allows for more malleable wound geometry and less risk of scar tissue formation.

The dimensions of the excision depend vastly on the location of the wound and the surrounding periwound tension. If the periwound is taught, the width of the apical excisional tissue base is narrower compared to flexible periwound with integumental overlap when the surrounding periwound is pinched together. On average, the base width of the apical excision has an average range of 1 mm-10 cm. The larger the diameter of the wound, the larger the base of the apical excision. The apical excision height is also within the same range measuring on average 3 mm-10 cm. The height of the apical excision depends on the size of the wound, the surrounding periwound tension and the location of the wound.

For instance, calcaneal wounds are typically larger in size, but the surrounding periwound tension is more taught compared to wounds that are located on the plantar surface of the ball of the foot. In this case, the excisional base width is narrower since the tension is restricting adequate tissue overlap. For larger wounds, such as sacral wounds, where the wound base encompasses greater surface area, the wound debridement base/height is 1 mm to 20 cm.

The general rule with this apical excisional wound debridement technique is to excise enough tissue that will allow the reduction of periwound tension to reapproximate the excisional borders (legs of the triangle) as demonstrates in FIG. 1.

Figure 4:
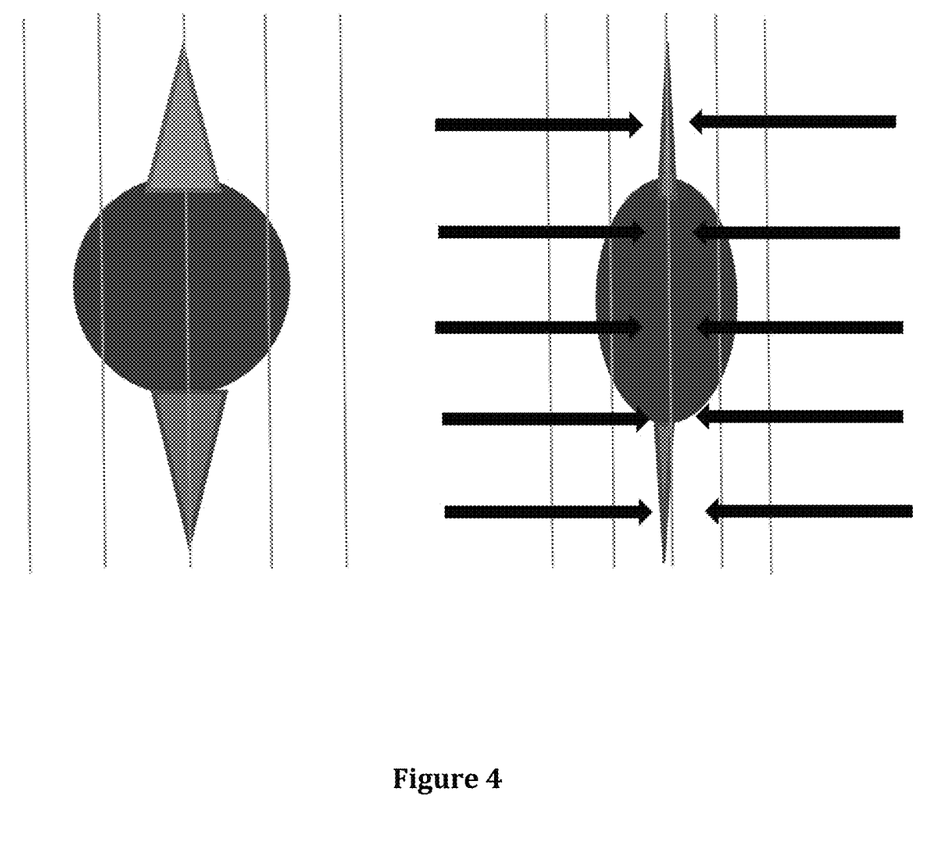
FIG. 4: Illustrates the excision in a wound relative to the skin lines and the suggested positioning of tension strips.

As seen in FIG. 4, two wedge excisions are taken from the extreme polar ends of the wound (parallel to the resting skin lines) as demonstrated in the left image in FIG. 4. The skin tension is flexible enough to allow approximation of the excisional borders, almost to the point where the apical excision appears like a linear incision when periwound tension is applied towards the wound, as demonstrated by the black arrows in the right image in FIG. 4. This linear manipulation of the original wedge excision acts as a seal that approximates the opposing skin edges which promotes epithelial cell migration in the newly excised tissue and original wound as well.

Figure 5:
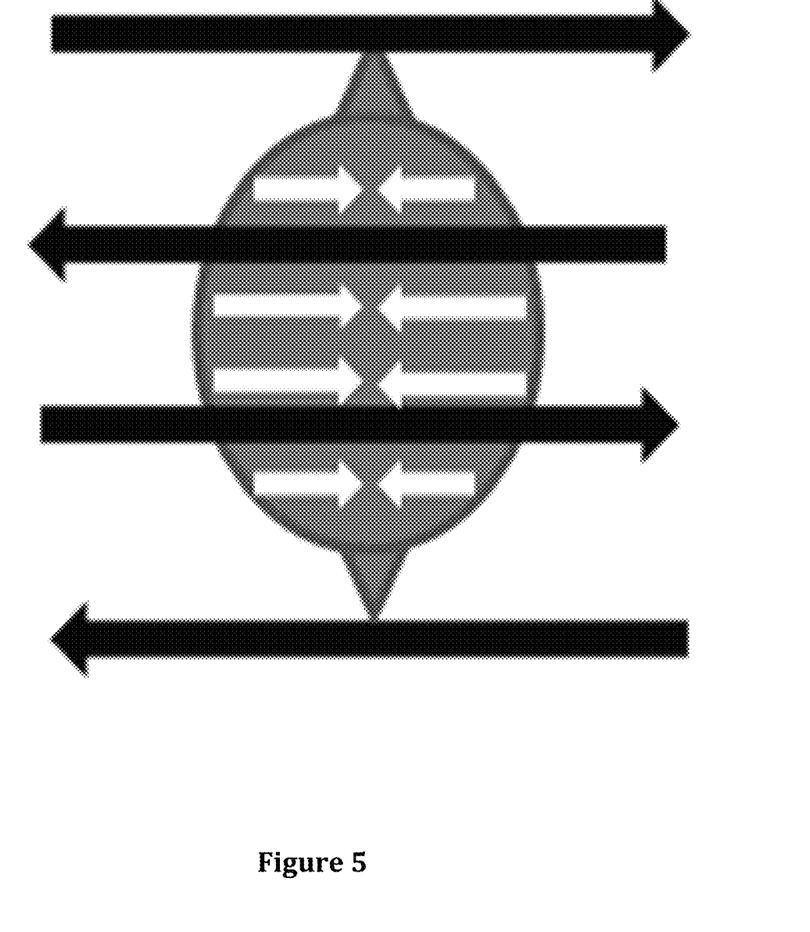
FIG. 5: Illustrates the bidirectional forces to be applied by the method of the present invention.

After apical wound debridement, it is beneficial to further reduce wound edge tension by applying bidirectional force towards the wound as represented by the large arrows in FIG. 5. Decreasing wound tensions along the perimeter of the wound allows the skin edges at the most extreme ends of the wound to be closely approximated which encourages epithelial cell migration, facilitating wound closure. This tension reduction is a component of the wound care treatment and dressing.

Provided below is a more detailed description of the examples of the invention. It is to be noted that the below-provided examples are illustrative of the invention and are not limitative of it.

EXAMPLE 1

Apical Debridement Examples

Five diabetic male patients with chronic wounds have apical wound debridement with the application of bidirectional tension towards the wound. Apical debridement is added to the original wound care treatment and a noticeable difference in wound geometry is noted and demonstrated in the photos of 5 male patients utilizing the methods of the present invention.

In FIG. 1, the dotted line represents the apex debridement at the two most extreme ends of a wound. Although there is more damage to the surrounding healthy and viable soft tissue, there is a geometrical benefit that transforms a circular wound to one that is more linear in nature.

Figure 2:
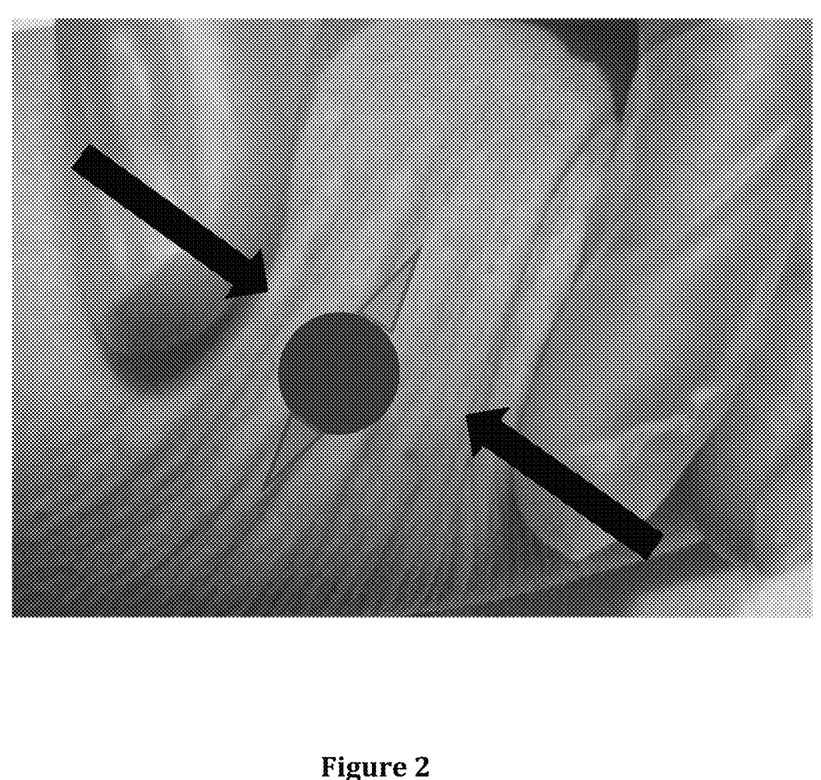
FIG. 2: Illustrates how to determine the natural flow of the integument lines.

In FIG. 2 is illustrated the second step in the present invention. After apical wound debridement, it is beneficial to further reduce wound edge tension by applying bidirectional force towards the wound as represented by the arrows. Decreasing wound tensions along the perimeter of the wound allows the skin edges at the most extreme ends of the wound to be closely approximated which encourages epithelial cell migration, facilitating wound closure.

Opposing tension application towards the wound using steristrip splinting further relaxed the wound edges and limited wound edge motion. Both the wound edge tension relaxation and limitation of movement demonstrated weekly wound measurement improvement and promoted integumental bridging within the wound itself compared to standard surgical wound debridement practices. Four out of the five subjects completely epithelialized by the end of this review and the fifth subject showed significant improvement in wound dimensions.

On average, the dimensions of the wound with apical surgical wound debridement show both visual changes in geometry and measurements. Clinically, the wounds demonstrate a change in shape with a more linear appearance. With this debridement and tension technique, it is common to see an increase in length dimension with a decrease in width dimension as the wound elongates with geometrical manipulation. With elongation of the wound bed, the skin edges come closer as the width measurements decrease. Over time, the polar edges of the wound adhere together and the wound heals from the polar edges towards the central aspect of the wound.

The combination of apical surgical wound debridement with wound tension reduction heals wounds at a faster rate compared to the standard of care debridement without taking tension into consideration.

Figure 6:
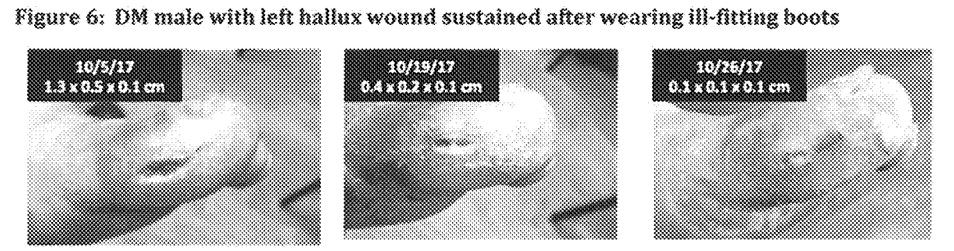
FIG. 6: Provides progress in method to treat a male with a left hallux wound.
Figure 7:
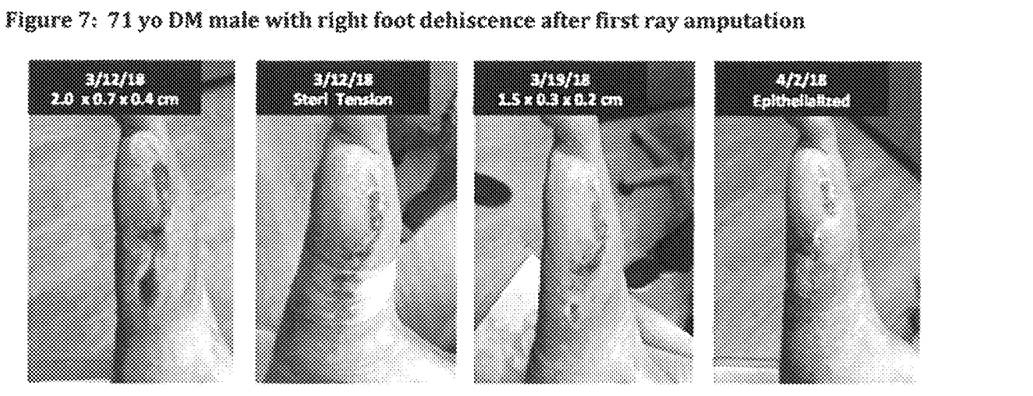
FIG. 7: Provides results of treating a male patient with the present incision after a first ray amputation.
Figure 8:
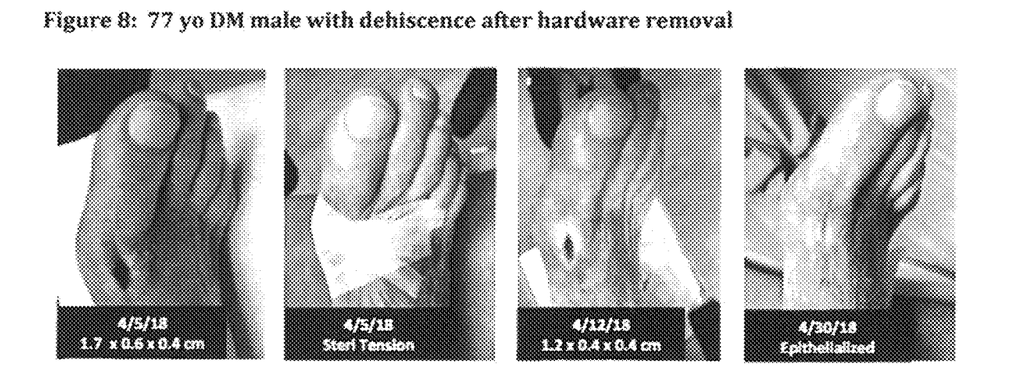
FIG. 8: Provides results when treating a male patient with a present invention in treating deficiencies after hardware removal.
Figure 9:
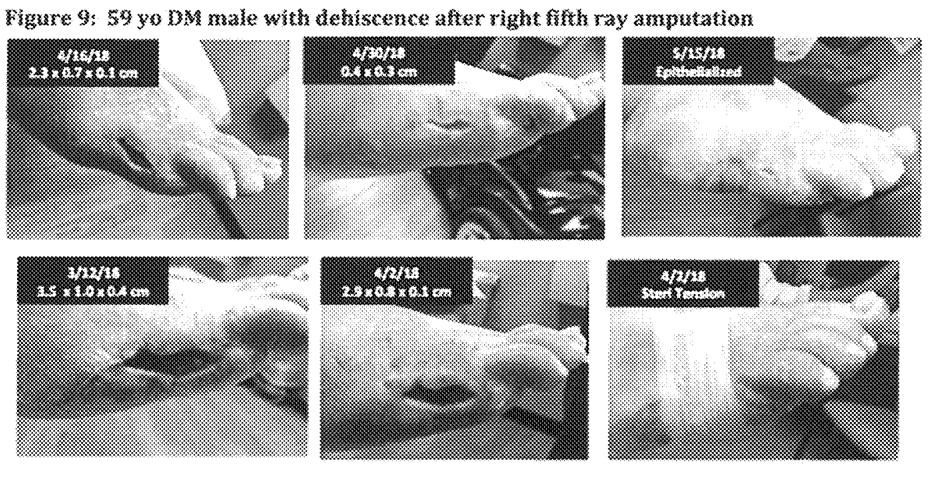
FIG. 9: Provides results when treating a right fifth ray amputation of a male patient when using the method of the present invention.
Figure 10:
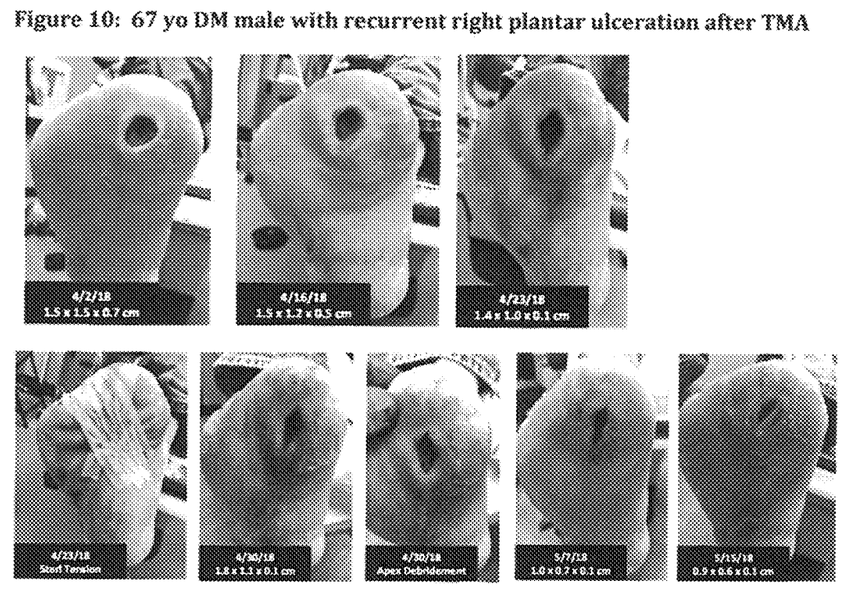
FIG. 10: Provides results in treating a male patient with recurrent plantar ulceration.

For instance, the patient in FIG. 6 had his first wound care consult in June 2017. He was undergoing treatment since his initial consult with monthly check up appointments. Apical surgical wound care debridement was initiated on Oct. 5, 2017. The patient underwent 5 treatments of apical surgical debridement and tension reduction in combination with his prior wound care and showed significant changes in wound measurements as seen in Table 1 below; he was completely epithelialized by the end of November.

TABLE 1

Wound measurements from initial wound care consult
Green: Patient underwent Apical Surgical Debridement/Wound
Tension Reduction Treatment from Oct. 5, 2017-Nov. 2, 2017 and
was documented as epithelialized on Nov. 27, 2017.

| | | | | |
|---|---|---|---|---|
| Lateral Left | Jun. 28, 2017 | 4.1 | 2.3 | 0.1 |
| Hallux | Jul. 3, 2017 | 4 | 2.5 | 0.1 |
| | Aug. 28, 2017 | 3 | 1.5 | 0.1 |
| | Sep. 4, 2017 | 3.1 | 1.2 | 0.2 |
| | Sep. 14, 20017 | 2.3 | 1 | 0.1 |
| | Sep. 22, 2017 | 2.2 | 0.8 | 0.1 |
| | Sep. 28, 2017 | 1.8 | 0.7 | 0.1 |

TABLE 1-continued

Wound measurements from initial wound care consult
Green: Patient underwent Apical Surgical Debridement/Wound
Tension Reduction Treatment from Oct. 5, 2017-Nov. 2, 2017 and
was documented as epithelialized on Nov. 27, 2017.

| | | | |
|---|---|---|---|
| Oct. 5, 2017 | 1.3 | 0.5 | 0.1 |
| Oct. 12, 2017 | 0.6 | 0.4 | 0.1 |
| Oct. 19, 2017 | 0.4 | 0.2 | 0.1 |
| Oct. 26, 2017 | 0.3 | 0.1 | 0.1 |
| Nov. 2, 2017 | 0.1 | 0.1 | 0.1 |
| Nov. 27, 2017 | Epithelialized | | |

EXAMPLE 2

The present invention relates to apical debridement is anatomically versatile and is applied to any well perfused wound on the body that would benefit from surgical wound debridement. This apical wound debridement technique better explains the reasoning and geometric advantage of apical excision and provides a more aggressive surgical debridement for both acute and chronic wounds. Apical wound debridement is a more detailed and valuable modification to the generic "surgical debridement" technique which has a limiting definition of debriding the wound bed and wound edges to the point of healthy bleeding tissue with preservation of the surrounding viable tissue.

Apical wound debridement techniques are used on their own without any other wound care products on acute wounds in healthy individuals. However, with chronic wounds, the healing process is significantly compromised needing the assistance of external wound care products along with effective wound debridement. Apical wound debridement is used in conjunction with multiple types of wound care products including collagen-based products, skin substitutes and topical wound products; as well as various reinforced skin closures.

Examples of skin substitute products used in conjunction with apical wound debridement include but are not limited to Epifix/EpiCord®, Amniofix/AmnioCord® by MiMedx, Dehydrated Human Amnion/Chorion Membrane (dHACM) Allograft PuraPly® by Organogenesis, Collagen matrix with the antimicrobial polyhexamethylene biguanide.

Furthermore, some examples of reinforced skin closures used in conjunction with apical wound debridement, include but are not limited to 3M Steristrips® (used in the case series presented above in the 5 subjects), PreLoc® system by ZipLine Medical.

Apical surgical wound debridement technique is used on its own without any other wound care products on acute wounds in healthy individuals. With Chronic wounds, the healing process is significantly compromised needing the assistance of external wound care products along with wound debridement. Apical surgical wound debridement has been used in conjunction with multiple types of wound care products including collagen-based products, acellular and cellular skin substitutes, biological skin substitutes and topical wound products; as well as various reinforced skin closures.

Examples of Skin Substitute Products Used in Conjunction with Apical Wound Debridement:

EpiFix®/EpiCord®, Amniofix®/AmnioCord® by MiMedx®
        Dehydrated Human Amnion/Chorion Membrane (dHACM) Allograft
    PuraPly®/Apligraf® by Organogenesis, Inc®
    Collagen matrix with the antimicrobial polyhexamethylene biguanide Examples of Reinforced Skin Closures Used in Conjunction with Apical Wound Debridement:

Steri-Strips® by 3M® (used in the case series presented above in the 5 subjects)
    PreLoc® system by ZipLine Medical®

Apical surgical wound debridement technique is used alone and includes but is not limited to be used in combination with the above mentioned registered trademarked wound care products/companies. There are multiple biological wound care dressings, acellular and cellular skin substitutes and wound care products on the market that are used with this method of debridement. Most of the wound care products include the "preparation of the wound bed" prior to product application. This includes surgical debridement of the wound edges as well as wound bed debridement of biofilm and non-viable tissue. Apical wound debridement is a modification of the standard of care surgical debridement and is used with any product that is on the market now or in the future that requires wound bed preparation including wound debridement prior to product application.

Other wound care companies that include both acellular and cellular skin substitutes, wound care dressings and other biologics that could be used in combination with apical debridement technique include:

Additional products from MiMedx®
    Additional products from Organogenesis, Inc® such as:
    PuraPly® Antimicrobial (PuraPly® AM)
    PuraPly®
    Affinity®
    NuShield®
    Apligraf®
    Dermagraft®
    Products from Osiris® Therapeutics
    Products from Biobrane®
    Products from Integra®
    Products from Biohorizons®
    Products from Transcyte®

EXAMPLE 3

This debridement technique is useful in conjunction with any wound care product or skin substitute as long as the patient is a candidate that tolerates surgical wound debridement with viable and adequate blood supply to the wound site. These wound products/skin substitutes adhere better to the wound base with wound debridement. These wound care products are thus better able to be more effective with this debridement/tension reduction technique due to the more aggressive nature of the debridement and the reduction of periwound tension. The application of reinforcement skin closure across the wound acts as a "wound splint" to prevent movement of the freshly formed epithelial cells, reduce periwound tension and reduce frictional forces that could potentially alter periwound tension and interfere with the viability of newly formed skin cells.

The positive effects of manipulating wound geometry using apical wound debridement and wound tension relief are not only useful for use in various wound types, but are not limited to the foot and ankle. These techniques are useful in conjunction with advanced wound care grafts, products and casting techniques. Apical debridement appears to be a valuable modification to the traditional wound debridement performed in practice today. The method with the use of wound tension relief has the power to expedite wound healing by increasing the number of chemical factors necessary for wound healing and by manipulating wound geometry.

Apical debridement is a valuable modification to the traditional wound debridement performed in practice today. This modification with the use of wound tension relief has the power to expedite wound healing by increasing the number of chemical factors necessary for wound healing and by manipulating wound geometry. Accelerating the healing time of wounds, decreases the risks of further complications including infection and amputation, decreases hospital costs and most importantly promotes a better patient quality of life.

Apical surgical wound debridement is a technique that is useful on any integumental wound on the body. This technique is illustrated on the five patients who demonstrated pedal wounds that were noted to be on the dorsal or plantar surface of the foot. Plantar pedal wounds are often a challenge to heal due to the fact that the plantar aspect of the foot is a weightbearing surface. Any weightbearing surface will undergo more pressure during gait and movement compared to non-weightbearing surfaces. Seeing that this technique manipulates wound geometry and facilitates wound closure on the plantar, weightbearing surface of the foot (a very challenging wound site to heal), this technique therefore manipulates and facilitates wound geometry to other body sites that demonstrate integumental wounds. These sites include and are not limited to the lower and upper extremities, back, chest, abdomen, neck and face. Besides diabetic pedal wounds, integumental wounds to any aspect of the body that are secondary to trauma such as lacerations, surgical wound dehiscence, pressure injuries, venous stasis, infection, benefit from the apical surgical wound debridement technique. Besides diabetic and venous ulcerations, pressure wounds are commonly seen in practice; such pressure injuries mostly affect the sacrum and back. If the patient has appropriate circulation to undergo such debridement, the same wound care used in the foot and ankle are applied. Regardless of the body site, the goal of wound care is to promote epithelial bridging between the distanced skin edges by manipulating the wound to a more linear shape, encourage epithelial cell migration among the peri-wound and perform the necessary wound care according to the type of wound.

The wounds are located anywhere on the body. For example, the foot, ankle and leg areas are often times locations for difficult to treat wounds. The method of the present invention is well suited to treating such areas of the body. However, the invention methods are not limited to only those areas hut have application to other wound locations. For instance, bed sores are often difficult to treat, but the uses of the present methods are useful to healing. Furthermore, ulcerations in any parts of the body benefit from the methods of the present invention.

REFERENCES

1. Brem H, Stojadinovic O, Diegelmann R F, et al. Molecular markers in patients with chronic wounds to guide surgical debridement. Mol Med. 2007; 13(1-2): 30-9.
2. https://musculoskeletalkey.com/cross-sectional-and-topographoc-anatomy/

What is claimed is:
1. A method of treating wounds, said method comprising:
   a. providing an apical debridement at wound edges;
   b. creating a wound geometry condusive to providing a malleable wound border;
   c. applying tension towards the wound from opposite directions.
2. The method according to claim 1 wherein the wound tension is manually provided followed by the use of steris-trips.
3. The method according to claim 2 wherein a length of the apical debridement is 1 mm to 10 cm.
4. The method according to claim 2, wherein a length of the apical debridement is 3 mm to 10 cm.
5. The method according to claim 2 wherein the wound is on the foot, ankle or leg.
6. The method according to claim 1 wherein a length of the apical debridement is 1 mm to 10 cm.
7. The method according to claim 1, wherein a height of the apical debridement is 3 mm to 10 cm.
8. The method according to claim 1, wherein the wound is on the foot, ankle, leg, back, chest, abdomen, neck or face.
9. The method according to claim 1, wherein the wound is a laceration, surgical wound dehiscence, pressure injury, venous stasis or infection.
10. A method for enhancing wound healing, said method comprising:
    a. providing an apical debridement wound edges;
    b. creating a wound geometry condusive to providing a malleable wound border; and
    c. applying tension towards the wound from opposite directions.
11. The method according to claim 10, wherein the wound tension is manually provided followed by the use of steris-trips.
12. The method according to claim 10, wherein a length of the apical debridement is 1 mm to 20 cm.
13. The method according to claim 10, wherein a length of the apical debridement is 1 mm to 10 cm.
14. The method according to claim 10, wherein theft height of the apical debridement is 3 mm to 10 cm.
15. The method according to claim 14, wherein a height of the apical debridement is 3 mm to 10 cm.
16. The method according to claim 10, wherein the wound is on the foot, ankle, leg, back, chest, abdomen, neck or face.
17. The method according to claim 10, wherein the wound is a laceration, surgical wound dehiscence, pressure inquiry, venous stasis or infection.
18. A method for advancing wound care grafts, said method comprising:
    a. providing an apical debridement wound edges;
    b. creating a wound geometry condusive to providing a malleable wound border; and
    c. applying tension towards the wound from opposite directions.
19. The method according to claim 18, wherein the wound tension is manually provided followed by the use of steris-trips.
20. The method according to claim 18, wherein a length of the apical debridement is 1 mm to 10 cm.
21. The method according to claim 18, wherein the length of the apical debridement is 1 mm to 10 cm.
22. The method according to claim 18, wherein a height of the apical debridement is 3 mm to 10 cm.
23. The method according to claim 22, wherein the apical debridement is 3 mm to 10 cm.
24. The method according to claim 18, wherein the wound is a bed sores.
25. The method according to claim 18, wherein the wound is an ulceration.

26. The method according to claim 18, wherein the wound is on the foot, ankle, leg, back, chest, abdomen, neck or face.

27. The method according to claim 18, wherein the wound is a laceration, surgical would dehiscence, pressure injury, venous stasis, or infection.

\* \* \* \* \*